(12) United States Patent
Bourgeois et al.

(10) Patent No.: US 10,716,927 B2
(45) Date of Patent: Jul. 21, 2020

(54) EXTRUDABLE TUBING FOR DELIVERY OF MEDICINAL FLUIDS

(71) Applicant: Tekni-Plex, Inc., Wayne, PA (US)

(72) Inventors: Philip D. Bourgeois, Perrysburg, OH (US); Joseph E. Olsavsky, Waterville, OH (US)

(73) Assignee: Tekni-Plex, Inc., Wayne, PA (US)

( * ) Notice: Subject to any disclaimer, the term of this patent is extended or adjusted under 35 U.S.C. 154(b) by 166 days.

(21) Appl. No.: 15/866,891

(22) Filed: Jan. 10, 2018

(65) Prior Publication Data

US 2018/0126145 A1     May 10, 2018

Related U.S. Application Data

(63) Continuation of application No. 14/448,432, filed on Jul. 31, 2014, now abandoned.

(51) Int. Cl.
*A61M 39/08*     (2006.01)
*B29C 65/48*     (2006.01)
(Continued)

(52) U.S. Cl.
CPC ......... *A61M 39/08* (2013.01); *B29C 65/4895* (2013.01); *B29C 66/1222* (2013.01); *B29C 66/1224* (2013.01); *B29C 66/5344* (2013.01); *B29C 66/71* (2013.01); *B29C 66/712* (2013.01); *B29C 66/723* (2013.01); *C08J 5/12* (2013.01); *A61M 2207/00* (2013.01); *B29C 65/565* (2013.01); *B29C 65/82* (2013.01); *B29C 66/73773* (2013.01); *B29K 2023/12* (2013.01);
(Continued)

(58) Field of Classification Search
CPC ........... A61M 2207/00; B29C 65/4895; B29C 65/565; B29C 65/82; B29C 66/1222; B29C 66/1224; B29C 66/5344; B29C 66/712; B29C 66/723; B29C 66/73773; B32B 37/0038; B32B 2038/168; C08J 5/12; B29L 2023/007; B29K 2105/0085
See application file for complete search history.

(56) References Cited

U.S. PATENT DOCUMENTS 6,927,258 B2 * 8/2005 Datta ...................... C08L 23/10
525/240
2004/0116609 A1    6/2004 Datta et al.
(Continued)

FOREIGN PATENT DOCUMENTS

CN     1486243     3/2004
EP     1275891 A1     1/2003
(Continued)

OTHER PUBLICATIONS

Office Action in corresponding EP Application No. 15747620.1 dated Mar. 29, 2017.
(Continued)

*Primary Examiner* — Nathan R Price
*Assistant Examiner* — Anh Bui
(74) *Attorney, Agent, or Firm* — Polsinelli, P.C.

(57) ABSTRACT

A flexible polymeric tube comprising:
    an outer tubular wall layer comprised of a thermoplastic propylene-based elastomer (PBE) material, and,
    an innermost tubular layer comprised of a thermoplastic ethylene-based olefinic material.

15 Claims, 5 Drawing Sheets

(51) Int. Cl.
  B29C 65/00   (2006.01)
  C08J 5/12    (2006.01)
  B29L 23/00       (2006.01)
  B29K 105/00      (2006.01)
  B29C 65/56       (2006.01)
  B29C 65/82       (2006.01)
  B29K 23/00       (2006.01)

(52) U.S. Cl.
  CPC . *B29K 2105/0085* (2013.01); *B29L 2023/007* (2013.01)

(56)           References Cited

U.S. PATENT DOCUMENTS

| | | | |
|---|---|---|---|
| 2005/0123703 A1* | 6/2005 | Ling | A61L 29/126 428/36.91 |
| 2007/0011951 A1 | 1/2007 | Gaeta et al. | |
| 2007/0015871 A1* | 1/2007 | Nakamura | A61L 29/041 525/88 |
| 2010/0137838 A1 | 6/2010 | Hwang | |
| 2013/0190244 A1* | 7/2013 | Borow | A61K 38/07 514/16.4 |
| 2013/0267636 A1 | 10/2013 | Satpathy et al. | |
| 2014/0079686 A1* | 3/2014 | Barman | A61K 8/4953 424/94.67 |

FOREIGN PATENT DOCUMENTS

| | | | | |
|---|---|---|---|---|
| EP | 1 353 793 A1 | 10/2003 | | |
| EP | 2186859 A1 | 5/2010 | | |
| EP | 2 599 470 A1 | 6/2013 | | |
| JP | 2001-001432 A | 1/2001 | | |
| JP | 2003 205033 A | 7/2003 | | |
| JP | 2009-522422 A | 7/2007 | | |
| JP | 4 561964 B2 | 10/2010 | | |
| JP | 2014-100895 A | 5/2014 | | |
| WO | WO-2006113132 A1 * | 10/2006 | ............. | C08L 23/10 |
| WO | 2007/077176 A1 | 7/2007 | | |
| WO | 2010 074896 A2 | 7/2010 | | |
| WO | 2014/081014 A1 | 5/2014 | | |

OTHER PUBLICATIONS

Response to Office Action in corresponding EP application 15747620.1 filed on Nov. 14, 2018.
Office Action in corresponding EP Application No. 15747620.1 dated Mar. 29, 2019.
Office Action in corresponding JP Application No. 2017-505503 dated Jul. 2019 (with English translation).
International Search Report and Written Opinion dated Oct. 1, 2015 in Int'l. Appln. No. PCT/US2015/039641.
McKeen, Laurence W., "Plastics Used in Medical Devices" Handbook of Polymer Applications in Medicine and medical Devices, Dec. 9, 2013, pp. 21-53, Elsevier.
Vistamaxx(TM) 3980FL Propylene-based Elastomer, ExxonMobil Chemical, downloaded from Internet Mar. 12, 2014 www.specialtyeastomers.com.
Vistamaxx(TM) 3020FL Propylene-based Elastomer, ExxonMobil Chemical, downloaded from Internet Mar. 12, 2014, www.specialtyeastomers.com.
Lopatin, et al., "Use of nonaqueous solvents to prepare injection solutions," Institute of Experimental and Clinical Oncology, Academy of Medicinal Sciences of the USSR, Moscow, Translated from Khimiko-Farmatsevticheskii Zhurnal, vol. 6, No. 11, pp. 36-37, Nov. 1972. Original article submitted Feb. 7, 1972.
Written Opinion of the Int'l. Preliminary Examining Authority dated Jun. 30, 2016 in corresponding Int'l. Appln. No. PCT/US2015/039641.
Int'l. Preliminary Report on Patentability dated Oct. 19, 2016 in corresponding application PCT/US2015/039641.
Thompson, "34 Bonding Plastics" from "Handbook of Adhesives," 1990, pp. 573-575.
Notice of Intention to Grant in corresponding EP Application No. 15747620.1 dated Jan. 2, 2020.
First Office Action in corresponding JP Application No. 2017-505503 dated Jul. 31, 2019 with English Translation.
First Examination Report in corresponding IN Application No. 201747005863 dated Oct. 30, 2019 with English Translation.
Second Office Action in corresponding CN Application No. 201580046314.8 dated Sep. 2, 2019 with English Translation.

* cited by examiner

EXTRUDABLE TUBING FOR DELIVERY OF MEDICINAL FLUIDS

FIELD OF THE INVENTION

The present invention relates to the composition, structure, assembly and method of making an extruded polymeric tube and bonding the tube in a co-axial arrangement with a pre-fabricated polymeric body (e.g., fitting) for delivery of fluids.

BACKGROUND

Plasticized polyvinyl chloride (PVC) tubing has been utilized in the medical field for many decades. Over this time period, there have been various post tube manufacturing operations utilized to apply fitments at the end of the tube so as to incorporate the tube into various medical assemblies, e.g., connected to an insulin pump or the like, or to a delivery member (e.g. needle set) for the delivery of fluids to a patient (human or other animal) for health maintenance or during operational procedures. Typically, these various fitments include a region where the tube is inserted into the fitment and it is then secured (e.g., by adhesives or other chemical and non-chemical bonding means) in liquid-tight engagement to the fitment. Fitments may be made from various materials, including acrylonitrile-butadiene-styrene (ABS) copolymers, polycarbonate (PC), acrylic resins and other thermoplastic materials so chosen for their mechanical properties, thermal stability and for the ability to be precisely molded within very tight dimensional tolerances.

During the assembly process of combining a tube with a fitment, there is a stage where a bonding material, such as a UV curable adhesive material, is applied with an applicator to the external outer surface of the tube, and the tube is then physically engaged into the fitment. At the conclusion of fitting the tube into the fitment, this portion of the assembly is exposed to UV (ultraviolet) light which activates the adhesive to cure into a final solid form and the tube is adhesively bonded to the fitment. The nature of the bonding which occurs is such that it takes a certain amount of force to physically remove the tube portion from the fitment, e.g., to prevent unintended dislodgement during use of the assembly. This force is typically much larger after the application and curing of the adhesive to the surfaces versus simply a physical insertion of the tube into the fitment, in the absence of the adhesive.

Plasticized PVC tubing has been demonstrated to be most useful for all of these operations with a variety of fitments made from the different materials types referenced above. However, for at least environmental, regulatory and/or legislative reasons, there is a need to avoid the use of plasticized PVC as the material with which to make medical tubing. The potential for migration of the plasticizer into the medicinal fluid has been cited as a concern for some fluid types.

Other elastomeric materials also have chemical functionality (esters, amide, etc.) that may have interactions with various medicinal fluids. Thus, there is a need to provide a secure bonding that does not require chemical functionality in the tube or fitment that may potentially interact with the fluid being delivered by the assembly.

Medicinal fluids—not just the solvent/fluid types, but the medicinal fluid itself, may comprise balanced/stable colloids and suspensions of the active pharmacological agents that are buffered with surfactants and other dispersion/suspending agents. These agents may preferentially adsorb to chemical functionalities of the tube material/luer and thus affect the medicinal efficacy of the fluid.

Still further, many of the common fitment materials (ABS, PC, and acrylics) are amorphous materials that are subject to crazing/cracking. Thus the ABS, PC, Acrylic, etc luers in common usage today may have molded in stress which makes them especially susceptible to cracking in the presence of solvents, either prior to or during use. The nature of the medicinal fluids may cause stress cracking of such amorphous materials or changes in dimensions of the luers that cause leakage or failure.

Thus, there is an ongoing need for new tubing and fitment assemblies that avoid the aforementioned problems of stress cracking, chemical interactions, and processing difficulties of the prior art.

SUMMARY OF THE INVENTION

The present invention contemplates the manufacture of an extruded tube, preferably a multilayer coextruded tube of at least two non-PVC containing polymeric materials (lacking chemical functionality) that are coextruded, whereby the tubing materials are bonded securely to each other and such that the outer tubing layer of the two materials can be readily and securely solvent bonded on an exposed outside surface to the inside surface of the central channel of a tubular component, such as a luer or other fitment. The tubing is particularly well adapted for bonding to a fitment comprised of inert polypropylene based materials for use in medical fluid delivery and treatment applications.

The present invention avoids the problems of the prior art plasticized PVC tubing, and also avoids the problems of using UV curable adhesives. These curable adhesives are expensive, and require the additional step of exposure to UV light, which adds considerably to the cost of assembling the tubing and fitment.

The invention further avoids the potential for fluid contamination. It has been observed that the fluid being injected through a tubing and fitment will often wet out the area of engagement between the tubing and fitment, thereby encountering the adhesive polymer material. The UV curable polymers may have extractable uncured monomer or other components that are not intended and would be detrimental to the patient if they become part of the injected fluids delivered to the patient.

The present invention further eliminates the need for the use of ester, urethane, or amide containing elastomers or other chemical functionality, such as carbonyls or acid groups, that may contact and interact with fluids being delivered through the tubing or fitment.

In accordance with one embodiment of the invention, the invention further avoids the use of fitment materials that are prone to stress cracking in the presence of medicinal fluids.

In accordance with one embodiment of the invention, a method is provided for coaxially bonding a polymeric tube to a prefabricated tubular body, the prefabricated tubular body defining a hollow central tubular passage having a longitudinal axis bounded by an inner wall of polypropylene based material, the method comprising:

extruding a mating polymeric tube having an outer tubular wall surface comprised of thermoplastic propylene-based elastomer (PBE) material, and a central tubular passage having a longitudinal axis and opposing ends, treating the outer surface of the mating tube along a selected axial length at one of the end of the tube with a solvent that causes the treated outer surface to adhere to the inner wall of the tubular body on drying, inserting the treated end of the mating tube coaxially into the central tubular passage of the tubular body such that the outer surface of the treated end mates with the inner wall of the tubular body along the selected axial length to form a mated juncture, allowing the mated juncture to dry such that the treated outer surface solvent bonds to the inner wall.

In one embodiment, the solvent is selected from one or more of cyclohexanone, cyclohexane, hexane, xylene, tetrahydrofuran (THF), ethyl acetate (EA) and methyl ethyl ketone (MEK).

In one embodiment, the solvent is selected from one or more of cyclohexane, cyclohexanone, xylene, tetrahydrofuran, and hexane.

In one embodiment, the PBE is a copolymer or blend of propylene and an alpha-olefin.

In one embodiment, the PBE is a propylene/alpha-olefin copolymer with semi-crystalline isotactic propylene segments.

In one embodiment, the PBE is a blend of a first polymer component (FPC) which is a predominately crystalline stereoregular polypropylene, and a second polymer component (SPC) which is a crystallizable copolymer of C2,C4-C20 alpha-olefin and propylene.

In one embodiment, the alpha-olefin is ethylene. The method of claim 1 wherein the tube has an inner wall comprising a layer of a polyethylene (PE).

In one embodiment, the PE of the inner wall is a low density polyethylene (LDPE), linear low density polyethylene (LLDPE), high density polyethylene (HDPE) or blends thereof.

In one embodiment, the step of extruding comprises coextruding an outer tubular layer of the PBE material with at least one innermost tubular layer of a thermoplastic ethylene-based olefinic material.

In one embodiment, the coextruded outer layer of the mating tube is the PBE with an ethylene content of at least 9% by weight and the innermost layer of the mating tube is polyethylene.

In one embodiment, the tubular body comprises a prefabricated body of PBE material.

In one embodiment, the PBE material of the tubular body is a homopolymer polypropylene or a copolymer of predominately propylene units and ethylene.

In accordance with another embodiment of the invention, a bonded tubular assembly is provided comprising:
 a prefabricated tubular body defining a hollow central tubular passage having a longitudinal axis bounded by an inner wall of propylene-based material,
 an extruded tube having an extruded outer tubular wall surface comprised of thermoplastic propylene-based elastomer (PBE) material, the mating tube having a central tubular passage having a longitudinal axis and opposing ends,
 wherein one of the ends of the mating tube is coaxially positioned within the central tubular passage of the prefabricated tubular body such that the outer surface of the one end of the mating tube is mated with the inner wall of the tubular body along a selected axial length of the mating tube,
 the mated outer surface and inner wall being solvent bonded to each other.

In one embodiment, the extruded tube is a coextruded tube having an outer tubular layer of the PBE material with at least one innermost tubular layer of a thermoplastic ethylene-based olefinic material.

In one embodiment, the coextruded outer layer of the mating tube is the PBE material with an ethylene content of at least 9% by weight and the innermost layer of the mating tube is polyethylene.

In one embodiment, the tube has an inner wall forming the central tubular passage comprising a coextruded a layer of a polyethylene (PE).

In one embodiment, the PE is a low density polyethylene (LDPE), linear low density polyethylene (LLDPE), high density polyethylene (HDPE) or blends thereof.

In accordance with one embodiment of the invention, a method is provided of delivering an aqueous based or non-aqueous based medicinal fluid or combination thereof to a patient comprising inserting a fluid delivery member into the body, the member being fluidly connected to the bonded tubular assembly, and delivering the medical fluid through the tube to the delivery member.

In one embodiment, the medicinal fluid comprises one or more of:
 the nonaqueous solvents selected from the group consisting of: vegetable oils, ethyl oleate, propylene glycol, and polyethylene glycols with molecular weights of 300 and 400.

In one embodiment, the medicinal fluid comprises one or more of:
 synthetic and semisynthetic preparations as solvent or mixed solvent based fluid preparations for injection to the patient, selected from the group consisting of alcohols, esters, ethers, amides, sulfoxides and pyrrolidones.

In one embodiment, the fluid preparations are selected form the group consisting of ethyl alcohol; benzyl alcohol; phenylethyl alcohol; propylene glycol; butylene glycol; trichloro-t-butyl; polyoxyethylene glycol; ethyl ether; phenoxyethanol; ethyl acetate ethyl oleate; benzyl benzoate; N-methylacetamide; N,N-dimethylacetamide; dimethyl sulfoxide (DMSO), and N-methyl 2-pyrrolidone, (NMP).

BRIEF DESCRIPTION OF THE DRAWINGS

The accompanying drawings illustrate one or more non-limiting examples of the invention.

DETAILED DESCRIPTION

Reference is made to the exemplary embodiments of the invention with reference to the Figures. Wherever possible, the same reference numbers are used throughout the drawings to refer to the same or like parts.

Figure 1:
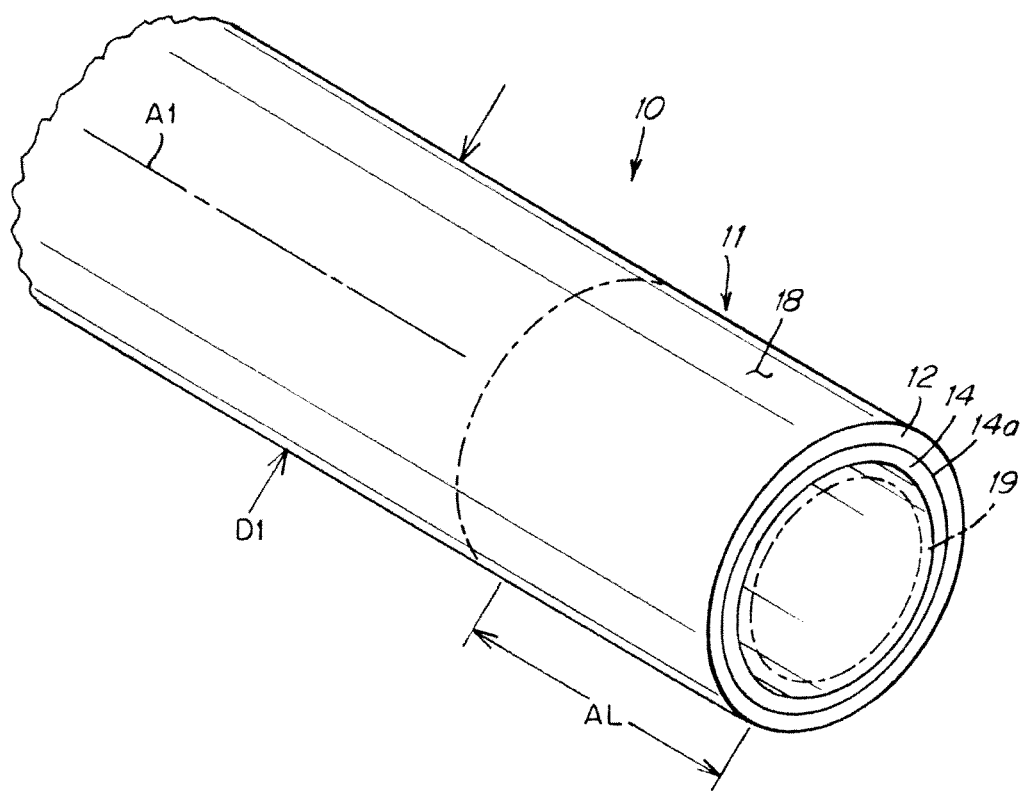
FIG. 1 is a schematic perspective view of a portion of a multilayer co-extruded tube according to one embodiment of the invention, the tube having a terminal end portion of a selected axial length AL.
Figure 2:
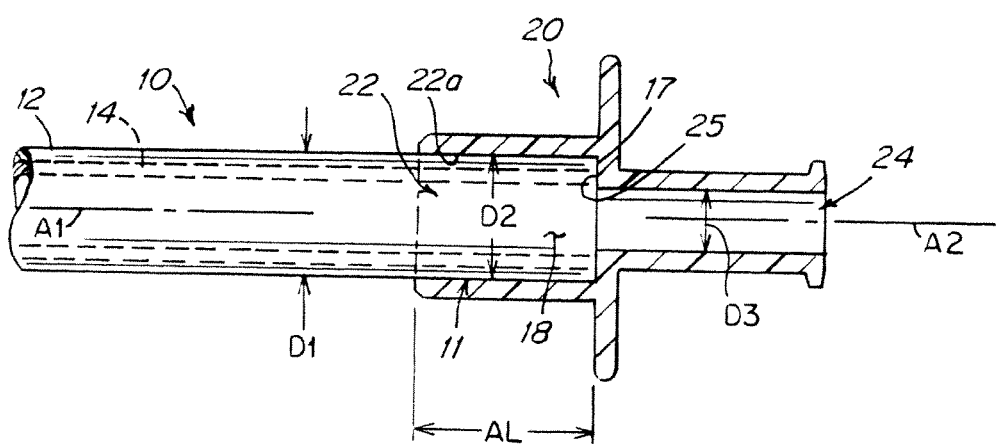
FIG. 2 is a side cross-sectional view of the tube of FIG. 1 with its terminal end portion coaxially inserted and solvent bonded within a central fluid flow channel end of a prefabricated tubular body (luer).
Figure 4:
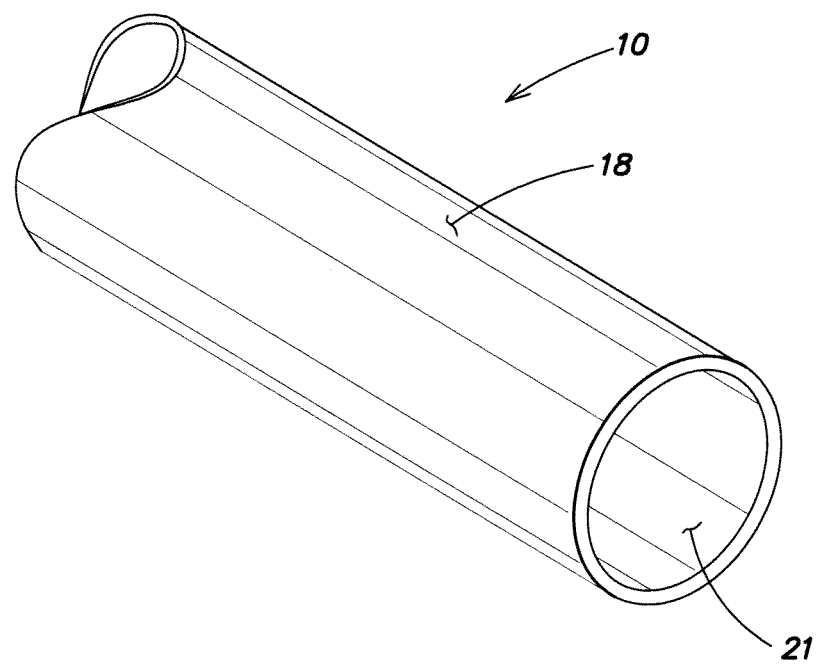
FIG. 4 is a schematic perspective view of a portion of a monolayer tube according to another embodiment of the invention.

With reference to FIGS. 1, 2 a polymeric tube 10 according to the invention is fabricated by co-extruding a first outer layer 12 comprised of an extrudable thermoplastic propylene-based elastomer (PBE) material into bonding engagement with the outer surface 14a of a first inner layer 14 comprised of an extrudable thermoplastic ethylene-based olefinic material. One or more additional intermediate or inner layers 19 of extrudable polymeric materials can, as optionally desired, be co-extruded together with the materials of layers 12, 14 into successive bonding engagement with the layers 12, 14 to form a three or more layered tube 10. Alternatively, a monolayer tube of the extrudable thermoplastic PBE (same material as outer layer 12) may be used as shown in FIG. 4 and described below.

The propylene-based outer layer 12 is typically selected to comprise a PBE that renders the material flexible for use as tubing for delivery of a medicinal fluid depending on the intended applications and also compatible with a propylene-based fitting (e.g., luer) to enable solvent bonding thereto. Suitable PBEs are described below.

In one embodiment, the present invention relates to a polymeric tube for the delivery of medicinal fluids comprising a propylene based elastomer (PBE) that exhibits substantially equivalent mechanical performance to plasticized PVCs known in the industry.

In one embodiment, the PBE polymers' composition of the present invention is propylene/alpha-olefin copolymers with semi-crystalline isotactic propylene segments. In one specific embodiment, the PBE for use in the present invention have a comonomer range of between 9 to 16%, preferably between 9 to 11%. The comonomers are alpha-olefins. In addition, the PBE polymers may have a narrow molecular weight distribution of 2-3. The molecular weight distribution is induced Mw/Mn (also referred to as polydispersity index or MWD).

In yet another embodiment, the suitable PBE for use in the present invention is Exxon Mobil Vistamaxx series (eg, 3020FL or 3980FL grades). One method of producing such a PBE is disclosed in U.S. Pat. No. 6,927,258, which is incorporated by reference herein. For examples, such a PBE is produced by blending a "first polymer component" ("FPC") which is a predominately crystalline stereoregular polypropylene with a "second polymer component" ("SPC") which is a crystallizable copolymer of C2, C4-C20 alpha-olefin (preferable ethylene) and propylene. Optional components of the blend are SPC2, a crystallizable copolymer of C2, C4-C20 alpha olefins (preferably ethylene). Other optional components are fillers, colorants, antioxidants, nucleating agents, lubricants and other process aids.

The FPC melts higher than 110 C (degrees Centigrade) and has a heat of fusion of at least 75 J/g (Joules/gram), as determined by DSC (Differential Scanning calorimetry) analysis. The crystalline polypropylene can be either a homopolymer or a copolymer with other alpha olefins. The SPC, and optionally the SPC2 if used, have stereoregular propylene sequences long enough to crystallize. The SPC has a melting point of less than 105 C and has a heat of fusion of less than 75 J/g. The SPC2 has a melting point of less than 115 C and has a heat of fusion of less than 75 J/g. One embodiment is blending isotactic polypropylene (FPC) with ethylene propylene copolymers (SPC) having about 4 wt % to about 35 wt % ethylene so as to ensure high compatibility with the FPC. The ratio of the FPC to the SPC of the blend composition may vary in the range 2:98 to 70:30 by weight.

In one embodiment, the PBEs of the present invention have a glass transition temperature (Tg) range of about −15 to −35 C. The PBE of the present invention have a melt flow range (MFR) as measured at 230 C of between 0.5 to 50 grams/10 minutes as per ASTM D1238. In one embodiment, the PBE of the present invention have a preferred Shore A hardness range of about 60 to 90 and have a flexural modulus range of about 500 to 20,000 psi (pounds per square inch) and more preferably of about 1,000 to 16,500 psi.

Alternatively, the outer layer may comprise a blend of polypropylene and other olefinic polymers (e.g., polyethylene or polyethylene-octene block copolymers); the blend should be extrudable and compatible with both the inner layer and the fitment to which it will be solvent bonded.

The thickness of outer layer 12 typically ranges between about 0.0005 inches and about 0.050 inches. The thickness of the outer layer will vary depending on cost of materials, desired physical properties, extrusion equipment, intended use of the tubing and fitment, and other design concerns.

The ethylene-based olefinic material of which the first inner layer 14 is comprised is preferably a predominately extrudable thermoplastic ethylene-based olefinic material. The inner layer may be comprised of a polyethylene ("PE"), typically a low density polyethylene ("LDPE"), linear low density polyethylene ("LLDPE"), high density polyethylene ("HDPE") or blends thereof. The inner layer is extrudable, compatible with adjacent tube layers, and where as it comprises the innermost layer that forms the fluid delivery channel, substantially inert and approved for use with the fluid. The thickness of the inner layer 14 typically ranges between about 0.0005 inches and about 0.025 inches but again will vary with overall tube dimensions and lengths, cost of materials, extrusion equipment, intended use (application), and other design concerns.

Both the first and second layer materials are thermoplastic materials that are extrudable, processable as a melt at elevated temperature, do not have significant creep, are of generally low modulus and are flexible materials that can be stretched repeatedly at room temperature with an ability to return to their approximate original length if not stretched beyond their elastic yield strain.

The inner layer 14 is non-polar and otherwise lacking chemical functionality (functional groups) that would interact with a medicinal fluid of the intended application. By medicinal fluid it is meant any aqueous based fluid, non-aqueous based fluid, or combination thereof acceptable for injection into a patient (human or other animal) which includes the active pharmacological substance or biological substance, the choice of which is for an intended beneficial medical treatment of the patient. The active pharmacological or biological substance to be injected (e.g., via subcutaneous or intramuscular introduction, intravenous and other parenteral means) may include but is not limited to insulin, anti-inflammatories, anti-septics, cancer therapies, arthritis therapies, other treatment therapies, protein and enzyme based pharmaceuticals, nutrients, and other medicants. The active pharmacological or biological substance may be delivered via any of various aqueous, nonaqueous, or mixed solvents and other carrier fluids. Of the nonaqueous solvents, the following are examples: vegetable oils, ethyl oleate, propylene glycol, and polyethylene glycols with molecular weights of 300 and 400. Synthetic and semisynthetic preparations are also available as solvent or mixed solvent based fluid preparations for injection to the patient; examples include the alcohols (e.g., ethyl, benzyl, phenylethyl, propylene glycol, butylene glycol, trichloro-t-butyl, etc.), ethers and esters (e.g., polyoxytheylene glycol, ethyl ether, phenoxyethanol, ethyl acetate ethyl oleate, benzl benzoate, etc.), amides (e.g., N-methylacetamide and N,N-dimethylacetamide), sulfoxides (e.g., dimethyl sulfoxide, (DMSO)), pyrrolidones (e.g., N-methyl 2-pyrrolidone, (NMP)) and the like.

The active pharmacological substance or biological substance is typically prepared as a stabilized mixture, suspension or emulsion in combination with the aqueous, nonaqueous or solvent based carrier fluid. Chemical interaction of the medicinal fluid with the chemical functionalities of the tube and fitment during conveyance to the patient, through adsorption or absorption of components of the medicinal fluid, is to be avoided as it may negatively affect the stability of the medicinal fluid and affect the proper administration of the active pharmacological substance or biological substance, thus negatively affecting the efficacy of the intended medical treatment of the patient.

The fitments must also not have any negative interaction with the medicinal fluid, either through direct solvation of the fitment by components of the medicinal fluid or through environmental stress cracking (ESC) of the fitment by the medicinal fluid. Solvation of the fitment by the medicinal fluid leads to loss of mechanical integrity of the fitment itself, decreases the bond strength between the tube and fitment during use and is also a means by which the dissolved fitment material may potentially be injected to the patient during fluid conveyance. Environmental stress cracking of the fitment leads to the mechanical failure of the fitment due to continuously acting external and/or internal stresses in the fitment due to the presence of surface active substances (known as stress cracking agents) that may exist in the form of surfactants, buffering agents or other suspending agents utilized to produce stable medicinal solutions and suspensions in which the fitment will come into contact with while in use. The ESC of the fitment may also contribute to a decrease of the bond strength between the tube and fitment. Although ESC results from the interaction of the polymer used to make the fitment with certain chemicals, it is usually not a chemical reaction between the polymer and the active environment and is well in known in the art. In practice, ESC occurs more readily in amorphous polymers such as ABS (acrylonitrile-butadiene-styrene terpolymers), PC (polycarbonate), PMMA (polymethyl methacrylate), PEMA (polyethyl methacrylate), PS (polystyrene), rigid PVC, SAN (styrene-acrylonitrile copolymer), all of which are commonly utilized as materials for fitments, as well as in some semi-crystalline thermoplastics like polyethylene. In the production of various fitments utilized in the medical field, injection molding is typically the process of choice and manufacturing necessity and there exists the potential for internally induced stresses in the final fitment due to the very high polymer melt injection pressures utilized in the injection molding process. Amorphous polymers (glassy polymers) exhibit a higher tendency for this type of failure because their loose structure facilitates fluid permeation into the polymer. The stress acting agents which may exist in the medicinal fluid may promote crazing, cracking or plasticization of the fitment. In amorphous polymers, crack formation due to ESC is often preceded by craze formation. Crazes are expanded regions held together by highly drawn fibrils which bridge the micro-cracks and prevent their propagation and coalescence. Semi-crystalline polymers such as PE show brittle fracture under stress if exposed to stress cracking agents. In such polymers, the crystallites are connected by the tie molecules through the amorphous phase. The tie molecules play a decisive role in the mechanical properties of the polymer, through the transmission of load. Stress cracking agents act to lower the cohesive forces which maintain the tie molecules in the crystallites, thus facilitating their "pull-out" and disentanglement from the lamellae.

in contrast, in accordance with the present invention, polypropylene is a material which is desirable for use as the fitment material as it has no known solvent at room temperature which may be utilized in a medicinal fluid, and polypropylene is a material in which ESC does not readily occur.

Returning to FIG. 2, the tubular body or fitment 20 to be solvent bonded to the tube 10 is typically formed into the configuration of a luer, plastic tube connector or other fitment that is used in medical applications such as for connecting tubes for delivery of medicinal fluids from a fluid source to a patient or receptacle in a sterile manner where the fluid is sealed within a closed system, the tubing and connector maintaining the fluid contained within the sealed system. The tubular body 20 is most preferably comprised of a prefabricated PBE material, utilizing either a homopolymer polypropylene or a copolymer of predominately propylene units and a compatible comonomer, such as ethylene. The polymeric material of which tubular body 20 is comprised can also have optional components such as fillers, colorants, antioxidants, nucleating agents, lubricants and other process aids.

As shown in FIGS. 1 and 2, the tube 10 has a terminal end portion 11 having an outer surface 18 and a selected axial length AL for purposes of insertion into passage 22 and solvent bonding to the inner wall surface 22a of the central fluid passage 22 of tubular body 20 (typically in the form of a luer). As shown in FIG. 2, the end portion 11 of the tube (after being coated with a solvent for bonding to the fitment 20) is inserted into passage 22 of body 20 such that axis A1 of the tube 10 is generally coaxially aligned with the axis A2 of the tubular body 20. The cross-sectional diameter D2 of the passage 22 is preferably complementary to the cross-sectional diameter D1 of the end portion 11 of the tube 10. The diameter D2 can be slightly smaller than D1 (e.g., 0.001 to about 0.015 inches smaller) in order to ensure a snug fit of the end portion 11 within passage 22. On insertion of end portion 11 into passage 22, the outer surface 18 engages against the inner surface 22a of passage 22 and the solvent that has been applied to surface 18 of tube end 11 prior to insertion is spread over both surfaces 18 and 22a along substantially the entire selected axial length AL.

The tubular body 20 typically has separate co-axially aligned (A1-A2) hollow central passage portions 22, 24 respectively that have different cross-sectional inner diameters D2 and D3, where D3 is typically smaller than D2 thus forming a stop surface 25 against which the larger diameter D1 terminal end surface 17 of the terminal end portion 11 of tube 10 (about the same or slightly larger than D2) is stopped and abuts against on forcible manual insertion of end portion 11 axially into and through passage 22.

The solvent for treating outer surface 18 of the tube 10 is typically selected from one or more hydrocarbons, such as cyclohexanone, cyclohexane, hexane, xylene, tetrahydrofuran (THF), ethyl acetate (EA) and methyl ethyl ketone (MEK). Solvent treatment typically comprises applying the solvent to surface 18 of the end portion 11 of tube 10 prior to inserting the end portion 11 into the axial passage 22 of the tubular body 20.

Figure 3:
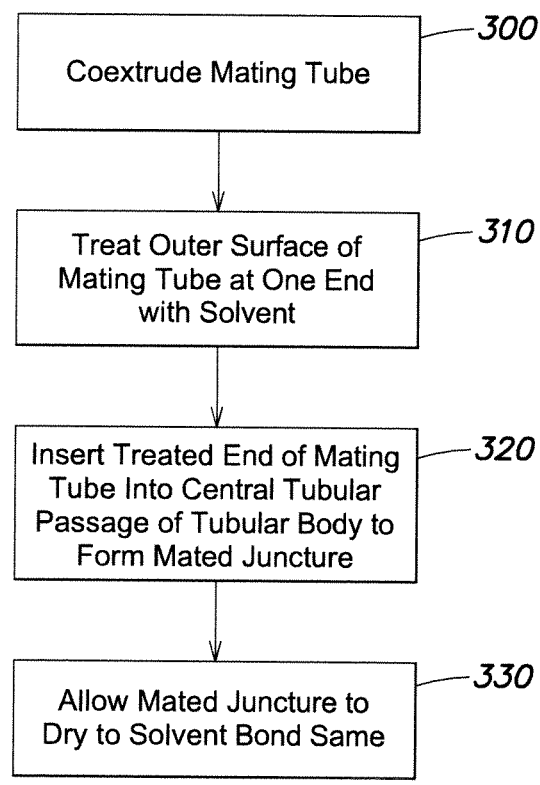
FIG. 3 is a schematic flow chart of one method according to the invention.

FIG. 3 is a flow chart illustrating one method embodiment of the invention. In the first step, a tube, such as multilayer tube 10 shown in FIGS. 1-2, is co-extruded as the mating tube to be solvent bonded with the tubular body 20. In a next step, the outer surface of the mating tube at one end portion is treated with solvent, e.g., by applying a coating of the solvent. In a next step, the treated end portion of the mating tube is inserted into a central tubular passage of the tubular body, to form a mated juncture along the coaxial mating portions of the outer surface of the tube and central passage of the tubular body. In a next step, the mated juncture is allowed to dry so that the solvent evaporates such that a solvent bond is formed between the mating portion of the outer surface of the tube and the central tubular passage of the tubular body.

In an alternative embodiment, shown in FIG. 4, a monolayer tube of the thermoplastic PBE material is provided. In this case, the single layer tubular wall forms both the outer surface 18 for solvent bonding with the central passage of the tubular body, and the inner tubular surface 21 of the single layer forms the fluid delivery passage that is intended, as previously described, to be non-polar and otherwise lacking in chemical functionality that would interact with a medicinal fluid of the intended application.

Tubing samples according to various multilayer embodiments were tested, as set forth below.

Tubing Test Samples:

Tubing specimens were fabricated by co-extrusion in multilayer form, with materials as specified below, and using an extrusion tooling such as the "Tri Die" extrusion apparatus manufactured by the Genca Division of General Cable Company, Clearwater, Fla.:

Outer Layer:

Vistamaxx 3980FL, or Vistamaxx 3020FL (Exxon Mobil Chemical, Houston, Tex., USA)

Inner Layer:

Westlake 808 LDPE (Westlake Chemical, Houston, Tex., USA)

Solvents tested:
  ethyl acetate (EA)
  methyl ethyl ketone (MEK)
  cyclohexanone
  tetrahydrofuran (THF)
  hexane
  xylene
  cyclohexane The two material, two layer (2M2L) coextruded tubing specimens were extruded with dimensions of: 0.152 inches OD×0.090 inches ID and overall wall thickness=0.031 inches. The outer layer of the PBE had a thickness of 0.026 inches and the inner layer of ethylene-based material had a thickness of 0.005 inches. As known in the art, the extrusion or co-extrusion process is carried out by melting the polymeric material(s), routing the melted material(s) under pressure through a suitable die head to form a tubular shaped extrudate or co-extrudate that is then cooled through conventional water baths or water vacuum tanks to form an end product. Tubing specimens so fabricated were then bonded to commercially available luers as specified below and then pull tested for bond strength. The test samples were prepared and test equipment and parameters utilized were as follows.

Samples Prepared for Solvent Bonding:
1. Tube samples were cut to 8 inches and the end of the tube was cleaned with 70% isopropyl alcohol and allowed to air dry.
2. Solvent was applied to ½ inch of the cleaned end of tube with small applicator and inserted into the luer.
3. Tubes were set to dry for 24 hours prior to mechanical testing (72° F./50% RH).

Mechanical Test Equipment and Parameters as described below were used in the testing of tubing samples that were solvent bonded to commercially available polypropylene luers. Mechanical test equipment which can test samples in a tensile manner and record forces on the sample are well known in the art; equipment such as those manufactured by Instron (826 University Avenue, Norwood, Mass., USA) or Lloyd Instruments Ltd (West Sussex, UK) are useful for testing. Such instruments include load cells attached to a moveable clamp and include an immovable clamp or jaw. Usually, a sample is clamped between the top and bottom clamps and one clamp is moved at a control rate and records the force which a sample is experiencing whilst the clamp is moving. In the test described below, the tube and luer assembly is secured within the equipment clamps and the maximum force, in pounds, to remove the tube from the luer is measured. Such a test is referred to as a pull test:

1. Test equipment clamps are set 3 inches apart.
2. Luer end of tube clamped in center of the upper clamp.
3. Loose end of tube clamped in center of the lower clamp.
4. The pull test is initiated and allowed to cycle through until the tube is pulled from luer at a rate of 12 inches per minute.
5. The pound force (pounds, lbs) to pull the tube from the luer is recorded and the tube is removed from the clamps.
6. Steps 1-5 are repeated for each sample (10×) for each type of luer/tube combination.

Commercially available luer specimens used in the assembly and pull tested were purchased from Qosina Inc., 150-Q Executive Drive, Edgewood, N.J. 11717, USA (Qosina.com) with the following identification and specifications: Part Number 65213, Female Luer Lock Connector, 0.145 inch to 0.156 inch ID, 0.206 inch OD, Material: Polypropylene.

Figure 5:
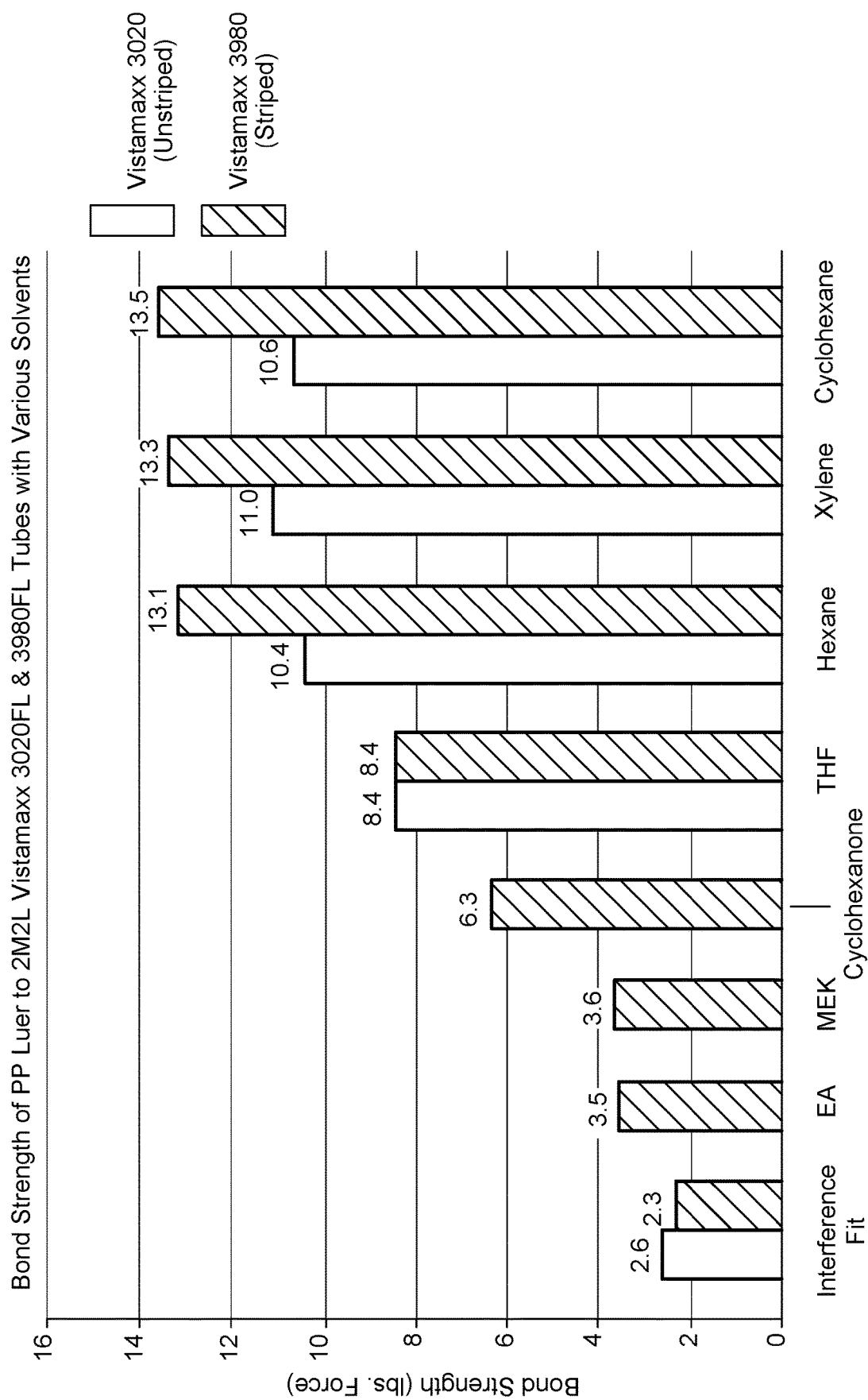
FIG. 5 is a graph of measured bond strength values for various embodiments of the invention utilizing different solvents for bonding the extruded tube and luer fitting, all showing a substantial improvement over an interference fit without solvent bonding.

As shown by the bond strength data summarized in FIG. 5, a multi-layer (2 material, 2 layer) tube 10 having an outer surface layer formed from the Vistamaxx™ 3980 FL (striped bars) or Vistamaxx™ 3020 FL (unstriped bars) that is solvent bonded to the least effective bonding solvent (ethyl acetate) still provides a significant improvement in bonding strength to a polypropylene luer, relative to a non-solvent bonded assembly that relies solely on a mechanical interference fit. As shown by the data, the bonding strength of the least effective solvent was at least about 3.5 lbs as compared with a bonding strength of about 2.3-2.6 lbs based on a mechanical interference fit alone (without solvent). A number of solvents produced bond strengths greater than 4 lbs., ranging from 6.3 to 13.5 lbs.

Figure 6:
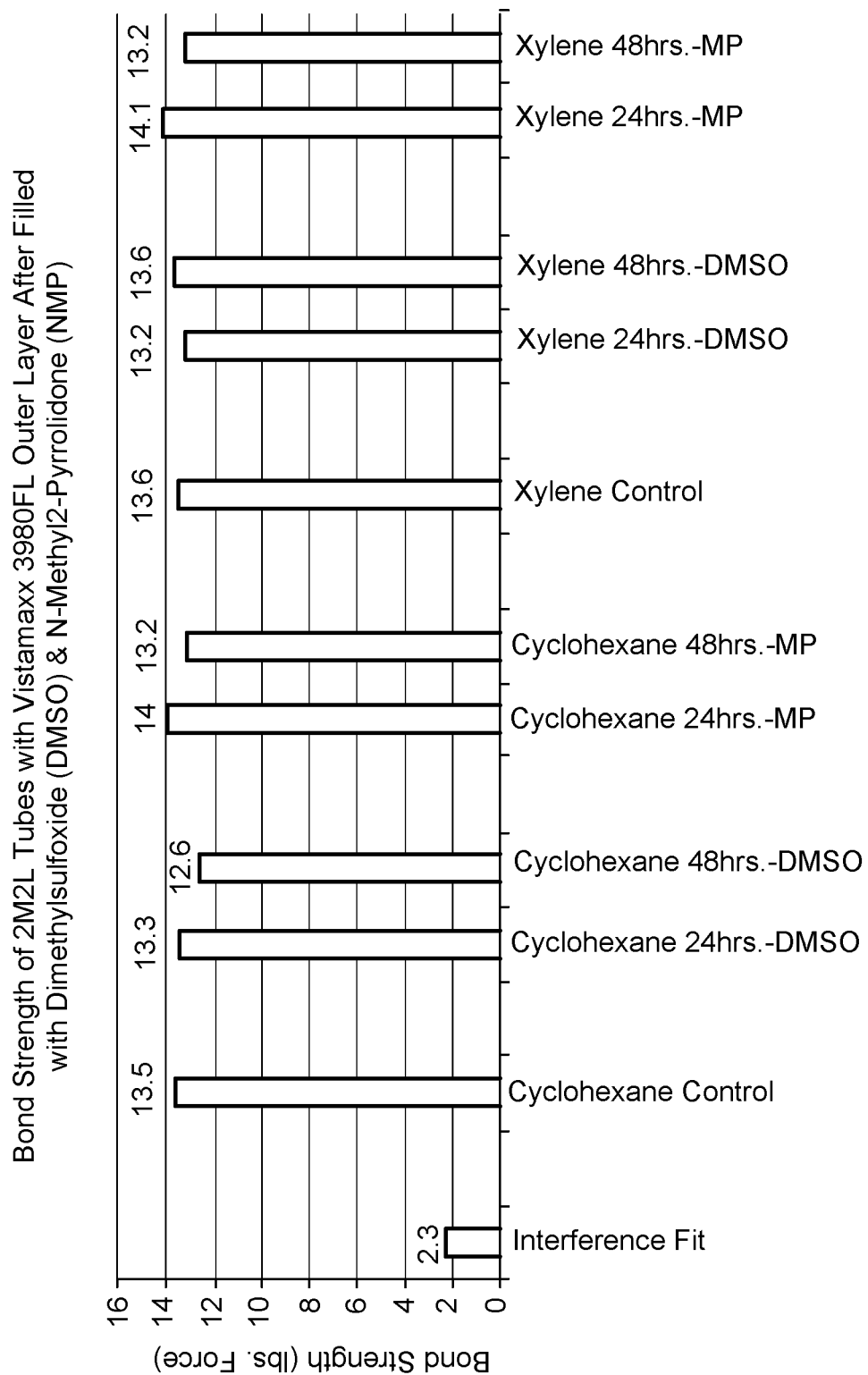
FIG. 6 is a graph similar to FIG. 5 showing significant improvements in bonding strength for co-extruded tubing samples filled with different fluids.

FIG. 6 demonstrates the chemical compatibility of two non-aqueous fluid systems, DMSO and NMP, respectively, with the aforementioned Vistamaxx 3980 FL tubing samples according to one embodiment of the invention. DMSO (dimethyl sulfoxide) and NMP (N-methyl 2-pyrrolidone) are common fluid carriers or solvents recognized by the US Food and Drug Administration for use in medicinal fluids and are typically utilized, amongst other uses, for solubilizing lipophilic pharmacological substances that are not readily soluble in water. DMSO and NMP are also recognized to be very aggressive to many polymers either as strong solvents or stress crack agents. The data presents the pull test results for samples made from Vistamaxx 3980FL as the outer layer, when coextruded with an inner layer of polyethylene, and solvent bonded to the polypropylene luer utilizing xylene or cyclohexane. After preparation of the tube and luer assembly, the luer was heat crimped to seal the luer at the end opposite to which the tube was inserted. After the luer end was sealed, the tube and luer assemblies were filled with either DMSO or NMP, and left at room temperature conditions (72 F/50% R.H.) in a sealed glass jar. At 24 hours and 48 hours after filling, the DMSO and NMP were drained from the tube and luer assemblies and the samples were pull tested. As can be seen in FIG. 6, there was little or no degradation of bond strength between the tube and luer over the stated time periods. There was no noted swelling of the tube and no swelling or cracking of the luer.

As is readily apparent, numerous modifications and changes may readily occur to those skilled in the art. Hence, the disclosure herein is not intended to limit the invention to the exact construction and operation shown and described. All suitable equivalents are included within the scope of the invention as claimed.

What is claimed is:

1. A method of coaxially bonding a polymeric tube (10) to a prefabricated tubular body (20), the prefabricated tubular body (20) defining a hollow central tubular passage (22) having a longitudinal axis bounded by an inner wall of polypropylene based material, the method comprising:
   extruding a mating polymeric tube (10) having an outer tubular wall surface (18) comprising thermoplastic propylene-based elastomer (PBE) material, and a central tubular passage having a longitudinal axis and opposing ends,
   treating the outer surface (18) of the mating tube (10) along a selected axial length at one of the end (11) of the tube (10) with a solvent that causes the treated outer surface (18) to adhere to the inner wall of the tubular body (20) on drying,
   inserting the treated end (11) of the mating tube (10) coaxially into the central tubular passage (22) of the tubular body (20) such that the outer surface (18) of the treated end (11) mates with the inner wall of the tubular body (20) along the selected axial length to form a mated juncture,
   allowing the mated juncture to dry such that the treated outer surface (18) solvent bonds to the inner wall,
   wherein the solvent is selected from one or more of cyclohexanone, cyclohexane, hexane, xylene, tetrahydrofuran (THF), ethyl acetate (EA) and methyl ethyl ketone (MEK) and wherein the PBE is a blend of a first polymer component (FPC) which is a predominately crystalline stereoregular polypropylene, and a second polymer component (SPC) which is a crystallizable copolymer of C2, C4-C20 alpha-olefin and propylene.

2. The method of claim 1 wherein the tube (10) has an inner wall comprising a layer (14) of a polyethylene (PE).

3. The method of claim 2 wherein the PE of the inner wall is a low density polyethylene (LDPE), linear low density polyethylene (LLDPE), high density polyethylene (HDPE) or blends thereof.

4. The method of claim 1 wherein the step of extruding comprises coextruding an outer tubular layer (12) of the PBE material with at least one innermost tubular layer (14) of a thermoplastic ethylene-based olefinic material.

5. The method of claim 4 wherein the coextruded outer layer (12) of the mating tube (10) is the PBE material with an ethylene content of at least 9% by weight and the innermost layer (14) of the mating tube (10) is polyethylene.

6. The method of claim 1 wherein the tubular body (20) comprises a prefabricated body of PBE material.

7. The method of claim 6 wherein the PBE material of the tubular body (20) is a homopolymer polypropylene or a copolymer of predominately propylene units and ethylene.

8. A bonded tubular assembly comprising:
   a prefabricated tubular body (20) defining a hollow central tubular passage (22) having a longitudinal axis bounded by an inner wall of propylene-based material,
   an extruded tube (10) having an extruded outer tubular wall surface (18) comprising thermoplastic propylene-based elastomer (PBE) material, the mating tube (10) having a central tubular passage having a longitudinal axis and opposing ends,
   wherein one of the ends (11) of the mating tube (10) is coaxially positioned within the central tubular passage (22) of the prefabricated tubular body (20) such that the outer surface (18) of the one end (11) of the mating tube (10) is mated with the inner wall of the tubular body (20) along a selected axial length of the mating tube (10),
   the mated outer surface (18) and inner wall being solvent bonded to each other,
   wherein the PBE is a blend of a first polymer component (FPC) which is a predominately crystalline stereoregular polypropylene, and a second polymer component (SPC) which is a crystallizable copolymer of C2, C4-C20 alpha-olefin and propylene.

9. The tubular assembly of claim 8 wherein the extruded tube (10) is a coextruded tube (10) having an outer tubular layer (12) of the PBE material with at least one innermost tubular layer (14) of a thermoplastic ethylene-based olefinic material.

10. The tubular assembly of claim 9 wherein the coextruded outer layer (12) of the mating tube (10) is the PBE material with an ethylene content of at least 9% by weight and the innermost layer (14) of the mating tube is polyethylene.

11. The tubular assembly of claim 8 wherein the tube (10) has an inner wall forming the central tubular passage comprising a coextruded layer of polyethylene (PE).

12. The tubular assembly of claim 11, wherein the PE is a low density polyethylene (LDPE), linear low density polyethylene (LLDPE), high density polyethylene (HDPE) or blends thereof.

13. A method of delivering an aqueous based or nonaqueous based medicinal fluid or combination thereof to a patient comprising inserting a fluid delivery member into the body, the member being fluidly connected to the bonded tubular assembly of claim 8, and delivering the medical fluid through the tube (10) to the delivery member.

14. The method of claim 13, wherein the medicinal fluid comprises one or more of:
   the nonaqueous solvents selected from the group consisting of: vegetable oils, ethyl oleate, propylene glycol, and polyethylene glycols with molecular weights of 300 and 400.

15. The method of claim 13, wherein the medicinal fluid comprises one or more of:
   synthetic and semisynthetic preparations as solvent or mixed solvent based fluid preparations for injection to the patient, selected from the group consisting of alcohols, esters, ethers, amides, sulfoxides and pyrrolidones, optionally wherein the fluid preparations are selected form the group consisting of ethyl alcohol; benzyl alcohol;
   phenylethyl alcohol; propylene glycol; butylene glycol; trichloro-t-butyl; polyoxyethylene glycol; ethyl ether; phenoxyethanol; ethyl acetate ethyl oleate; benzyl benzoate; N-methylacetamide; N,N-dimethylacetamide; dimethyl sulfoxide (DMSO), and N-methyl 2-pyrrolidone (NMP).

* * * * *